(12) United States Patent
Olovsson et al.

(10) Patent No.: US 10,302,603 B2
(45) Date of Patent: May 28, 2019

(54) ROTARY VALVE

(71) Applicant: GE Healthcare Bio-Science AB, Uppsala (SE)

(72) Inventors: Bjorn Olovsson, Uppsala (SE); Thomas Arctaedius, Uppsala (SE)

(73) Assignee: GE Healthcare Bio-Science AB, Uppsala (SE)

( * ) Notice: Subject to any disclaimer, the term of this patent is extended or adjusted under 35 U.S.C. 154(b) by 240 days.

(21) Appl. No.: 15/104,069

(22) PCT Filed: Dec. 15, 2014

(86) PCT No.: PCT/SE2014/051499
§ 371 (c)(1),
(2) Date: Jun. 13, 2016

(87) PCT Pub. No.: WO2015/094095
PCT Pub. Date: Jun. 25, 2015

(65) Prior Publication Data
US 2016/0313289 A1    Oct. 27, 2016

(30) Foreign Application Priority Data
Dec. 19, 2013  (SE) ...................................... 1351525

(51) Int. Cl.
  *G01N 30/20*   (2006.01)
  *G01N 30/46*   (2006.01)
  (Continued)

(52) U.S. Cl.
  CPC ............ *G01N 30/20* (2013.01); *F16K 11/076* (2013.01); *F16K 11/078* (2013.01);
  (Continued)

(58) Field of Classification Search
  CPC ............. G01N 30/20; G01N 2030/202; B01D 15/1842; B01D 2215/024; F16K 11/0743
  See application file for complete search history.

(56) References Cited

U.S. PATENT DOCUMENTS

| 4,614,204 A | 9/1986 | Dolejs |
| 4,632,149 A | 12/1986 | Oroskar et al. |

(Continued)

FOREIGN PATENT DOCUMENTS

| JP | 2010216636 A | 9/2010 |
| WO | 2001/40688 A2 | 6/2001 |

(Continued)

OTHER PUBLICATIONS

International Preliminary Report on Patentability Received for PCT Patent Application No. PCT/SE2014/051499, dated Jun. 21, 2016, 6 pages.

(Continued)

*Primary Examiner* — David Z Huang
(74) *Attorney, Agent, or Firm* — Wood IP LLC

(57) ABSTRACT

A rotary valve comprising a stator and a rotor, wherein the stator comprises at least three primary connection ports and at least three secondary connection ports, and wherein rotor interconnection paths are arranged to in the different rotor positions interconnect the primary connection ports with the secondary connection ports such that all of at least three secondary connection ports can be connected one at the time to each of at least three primary connection port by rotating the rotor into the different rotor positions.

A chromatography system comprising at least three chromatography columns and a column inlet rotary valve, a column outlet rotary valve and a feed recirculation flow path.

20 Claims, 10 Drawing Sheets

(51) Int. Cl.
*F16K 11/074* (2006.01)
*F16K 11/076* (2006.01)
*F16K 11/078* (2006.01)
*B01D 15/18* (2006.01)

(52) U.S. Cl.
CPC ........ *F16K 11/0743* (2013.01); *G01N 30/467* (2013.01); *G01N 30/468* (2013.01); *B01D 15/1821* (2013.01); *G01N 30/466* (2013.01); *G01N 2030/201* (2013.01); *G01N 2030/202* (2013.01)

(56) References Cited

U.S. PATENT DOCUMENTS

| | | | | |
|---|---|---|---|---|
| 4,705,627 | A * | 11/1987 | Miwa | B01D 15/1842 137/625.46 |
| 6,012,487 | A * | 1/2000 | Hauck | F16K 11/0743 137/625.11 |
| 6,372,127 | B1 * | 4/2002 | Ikeda | B01D 15/1842 210/264 |
| 6,672,336 | B2 * | 1/2004 | Nichols | F16K 11/074 137/625.11 |
| 8,349,175 | B1 | 1/2013 | Oroskar et al. | |
| 8,656,955 | B2 * | 2/2014 | Price | F16K 11/074 137/625.15 |
| 2011/0240899 | A1 * | 10/2011 | Wilen | F16K 11/0743 251/304 |
| 2012/0103887 | A1 * | 5/2012 | Maeda | F16K 11/0743 210/198.2 |
| 2013/0068977 | A1 | 3/2013 | Picha et al. | |
| 2016/0305916 | A1 * | 10/2016 | Olovsson | B01D 15/1842 |

FOREIGN PATENT DOCUMENTS

| | | |
|---|---|---|
| WO | 2001/40688 A3 | 11/2001 |
| WO | 2003/026772 A2 | 4/2003 |
| WO | 2003/026772 A3 | 12/2003 |
| WO | 2008/103097 A1 | 8/2008 |
| WO | 2008140374 A1 | 11/2008 |
| WO | 2010056189 A1 | 5/2010 |
| WO | 2011146861 A1 | 11/2011 |
| WO | 2014031069 A1 | 2/2014 |
| WO | 2015/094095 A1 | 6/2015 |

OTHER PUBLICATIONS

Extended European Search Report Received for European Patent Application No. 14871499.1, dated May 23, 2017, 8 pages.
Chinese Office Action Received for Chinese Patent Application 201480069396.3 dated Dec. 1, 2017, 12 Pages (6 pages Official Copy + 6 Pages English Translation).
International Search Report and Written Opinion regarding International Application No. PCT/SE2014/051499, dated Mar. 19, 2015, 12 pages.
International-Type Search Report regarding SE Application No. SE 1351525-9, dated Jul. 2, 2014, 6 pages.

* cited by examiner

ROTARY VALVE

CROSS-REFERENCE TO RELATED APPLICATIONS

This application is a filing under 35 U.S.C. 371 of international application number PCT/SE2014/051499, filed Dec. 15, 2014, which claims priority to SE 1351525-9 application number, filed Dec. 19, 2013, the entire disclosures of each of which are hereby incorporated by reference.

FIELD OF THE INVENTION

The present invention relates to valves and more specifically to rotary valves.

BACKGROUND

Valves are commonly used in devices that involve the transportation of a fluid. A typical type of valve, for example used in laboratory systems of moderate sizes, is the rotary valve.

Generally, a rotary valve has a stationary body, herein called a stator, which co-operates with a rotating body, herein called a rotor.

The stator is provided with a number of inlet and outlet ports. The ports are via bores in fluid communication with a corresponding set of orifices on an inner stator face. The inner stator face is an inner surface of the stator that is in fluid tight contact with an inner rotor face of the rotor. The rotor is typically formed as a disc and the inner rotor face is pressed against the inner stator face in rotating co-operation. The inner rotor face is provided with one or more grooves which interconnect different orifices depending on the rotary position of the rotor with respect to the stator.

Rotary valves can be designed to withstand high pressures (such as pressures above 25 MPa). They can be made from a range of materials, such as stainless steel, high performance polymeric materials and ceramics.

The number of inlets/outlets as well as the design of grooves in the rotor or the stator reflects the intended use of a specific valve. A common type of multi-purpose valve has one inlet port (typically placed in the rotary axis of the valve) and a number of outlets ports that are placed equidistantly around the inlet port. The rotor has a single, radially extending groove that has one end in the rotary centre, thereby always connecting to the inlet, while the other end connects to any one of the outlets depending on the angular position of the rotor with respect to the stator. Such a valve is useful to direct a flow from the inlet to any of the outlets—one at a time.

In chromatography systems for continuous chromatography, such as simulated moving bed systems usually a large number of valves are used for providing feed and buffer to the different columns in the system in correct order. There is a need for better valve arrangements in such systems.

SUMMARY OF THE INVENTION

One object of the invention is to provide a rotary valve that can be used for continuous chromatography.

A further object of the invention is to provide a continuous chromatography system with convenient and effective valve arrangement.

This is achieved in a rotary valve comprising a stator with an inner stator face, and a rotor with an inner rotor face arranged in sealing contact with the inner stator face, the rotor is rotatably movable to a plurality of rotor positions about a rotational axis relative to the inner stator face, the stator comprises a plurality of connection ports each being in fluidic contact with a corresponding valve orifice at the inner stator face and the rotor comprises two or more rotor interconnection paths for selective fluidic interconnection of said valve orifices with respect to the rotor position, wherein the stator comprises at least three primary connection ports and at least three secondary connection ports, and wherein the rotor interconnection paths are arranged to:

in the different rotor positions interconnect the primary connection ports with the secondary connection ports such that all of at least three secondary connection ports can be connected one at the time to each of at least three primary connection port by rotating the rotor into the different rotor positions.

This is also achieved in a chromatography system comprising at least three chromatography columns, said system further comprising:

a column inlet rotary valve as defined above connected to the inlets of at least three columns in the system and to at least three inflows and a column outlet rotary valve as defined above connected to the outlets of at least three columns in the system and to at least three outflows, and a feed recirculation flow path in which feed recirculation from the outlet of the column presently serving as primary load column in a chromatography process to the inlet of the column presently serving as secondary load column is transferred, wherein said feed recirculation flow path transfers the feed recirculation from all the columns in the system serving as primary load columns and wherein said feed recirculation flow path is connected to the inlets and outlets of the columns through the column inlet and column outlet rotary valves.

Hereby at least three columns and at least three inflows can be connected to the rotary valve and the rotary valve can connect the inflows to any one of the columns. This can be used in a chromatography system. This will provide a flexible rotary valve for use in for example a simulated moving bed chromatography system. Hereby a chromatography system with inlet and outlet rotary valves and feed recirculation can be provided. This will give a system with fewer valves and fewer flow connections compared to traditional simulated moving bed chromatography systems. This will provide a convenient and improved rotary valve and chromatography system.

In one embodiment of the invention the interconnections of the primary connection ports with the secondary connection ports will be shifted according to a simulated moving bed process by rotating the rotor.

In one embodiment of the invention at least two of the rotor interconnection paths are partly bending grooves.

In one embodiment of the invention the rotor interconnection paths are arranged to:

in a first rotor position interconnect a first primary valve orifice with a first secondary valve orifice, a second primary valve orifice with a second secondary valve orifice, a third primary valve orifice with a third secondary valve orifice and a fourth primary valve orifice with a fourth secondary valve orifice.

in a second rotor position interconnect the first primary valve orifice with the fourth secondary valve orifice, the second primary valve orifice with the first secondary valve orifice, the third primary valve orifice with the second secondary valve orifice and the fourth primary valve orifice with the third secondary valve orifice, in a third rotor position interconnect the first primary valve orifice with the third secondary valve orifice, the second primary valve orifice with the fourth secondary valve orifice, the third primary valve orifice with the first secondary valve orifice and the fourth primary valve orifice with the second secondary valve orifice, in a fourth rotor position interconnect the first primary valve orifice with the second secondary valve orifice, the second primary valve orifice with the third secondary valve orifice, the third primary valve orifice with the fourth secondary valve orifice and the fourth primary valve orifice with the first secondary valve orifice.

In one embodiment of the invention at least two of the rotor interconnection paths comprise one circular groove and one radial channel.

In one embodiment of the invention the circular grooves are concentrically positioned around the centre of the rotary valve and have different radius corresponding to the different radius at which the secondary valve orifices are provided and the radial channels are provided reaching out from their respective circular grooves to the positions of the primary valve orifices.

In one embodiment of the invention extra primary connection ports and valve orifices are provided in the stator in order to allow column bypass and/or additional set up of columns.

In one embodiment of the chromatography system inlets of said chromatography columns are connected one to each of said primary connection ports of the inlet rotary valve and outlets of said chromatography columns are connected one to each of said primary connection ports of the outlet rotary valve and said inflows are connected one to each of said secondary connection ports of the inlet rotary valve and said outflows are connected one to each of said secondary connection ports of the outlet rotary valve and wherein said rotor interconnection paths are provided such that each of at least three inflows can be connected one at the time with each of at least three column inlets through the inlet rotary valve and each of at least three outflows can be connected one at the time with each of at least three column outlets through the outlet rotary valve and by rotating the rotors the inflows to the column inlets and the outflows to the column outlets will be shifted according to a simulated moving bed process.

In one embodiment of the chromatography system the feed recirculation flow path comprises a detector. Hereby the number of detectors in the system can be decreased compared to traditional simulated moving bed systems.

BRIEF DESCRIPTION OF THE DRAWINGS

FIG. 3a shows a rotary valve according to one embodiment of the invention that can be used in the chromatography system of FIG. 2a.

FIGS. 4a,b,c,d show the four different rotor positions of the rotary valve shown in FIG. 3a.

DETAILED DESCRIPTION OF EMBODIMENTS OF THE INVENTION

Figure 1:
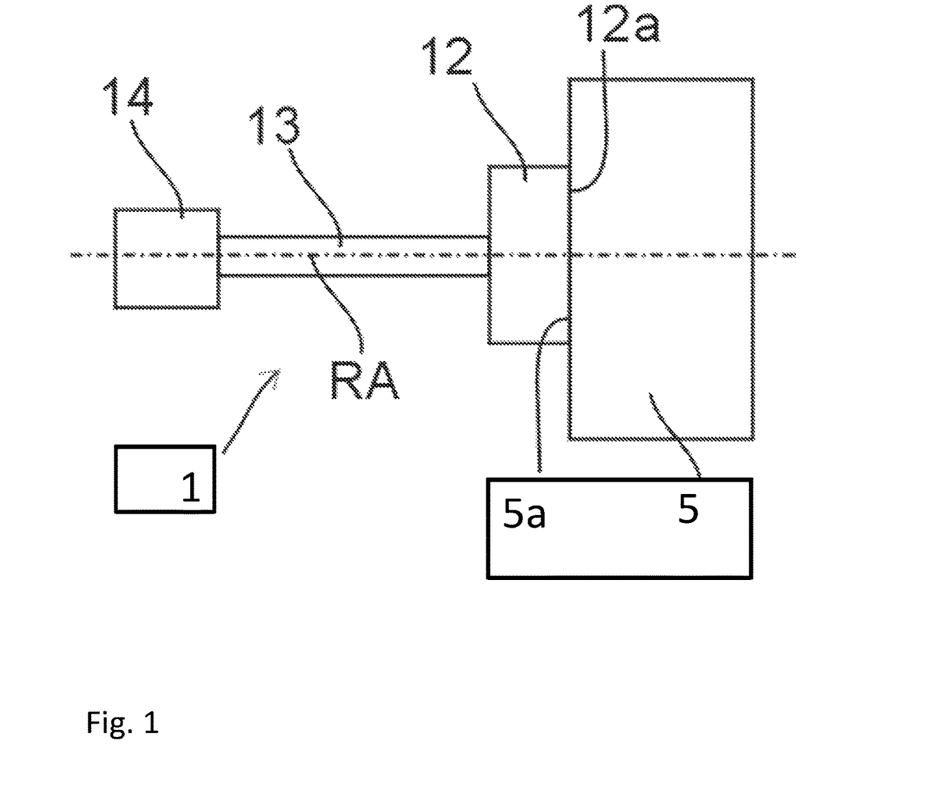
FIG. 1 is a schematic side view of a rotary valve according to one embodiment of the present invention.

The main parts of a typical rotary valve 1 are schematically shown in FIG. 1 (wherein no brackets or similar load carrying or fastening elements are shown). The rotary valve 1 has a stator 5, a rotor 12, a rotary shaft 13 that optionally may be provided with means (not shown) for recognizing its angular position and a driving unit 14 typically comprising a gear box and a motor (although a valve also may be operated manually). The rotor is rotatable with respect to the stator around a rotary axis RA of the valve.

The stator 5, which is fixed with respect to the instrument into which it is built, is provided with ports for fluid communication with a fluid source/outlet and any component with which the valve is to co-operate. The ports may be positioned on any suitable part of the stator, and in any suitable direction. The ports are provided with means to connect capillaries or tubing. Such means may be of any suitable type, such as conventional Valco fittings well known to anyone skilled in the art. The ports are via channels in fluid communication with a corresponding set of valve orifices on an inner stator face 5a, i.e. the surface of the stator that during operation is in contact with the rotor 12.

The rotor 12 is typically formed as a disc and has an inner rotor face 12a that is pressed against the flat inner stator face 5a during operation to achieve sealing contact there between. The inner rotor face 12a is provided with one or more interconnection paths which interconnect different valve orifices of the inner stator face 5a depending on the rotary position of the rotor with respect to the stator. The interconnection paths may be any type of path capable of providing fluidic contact between two valve orifices, and may be comprised of an internal channel with discrete orifices, grooves in the inner rotor face or the like.

Figure 2A:
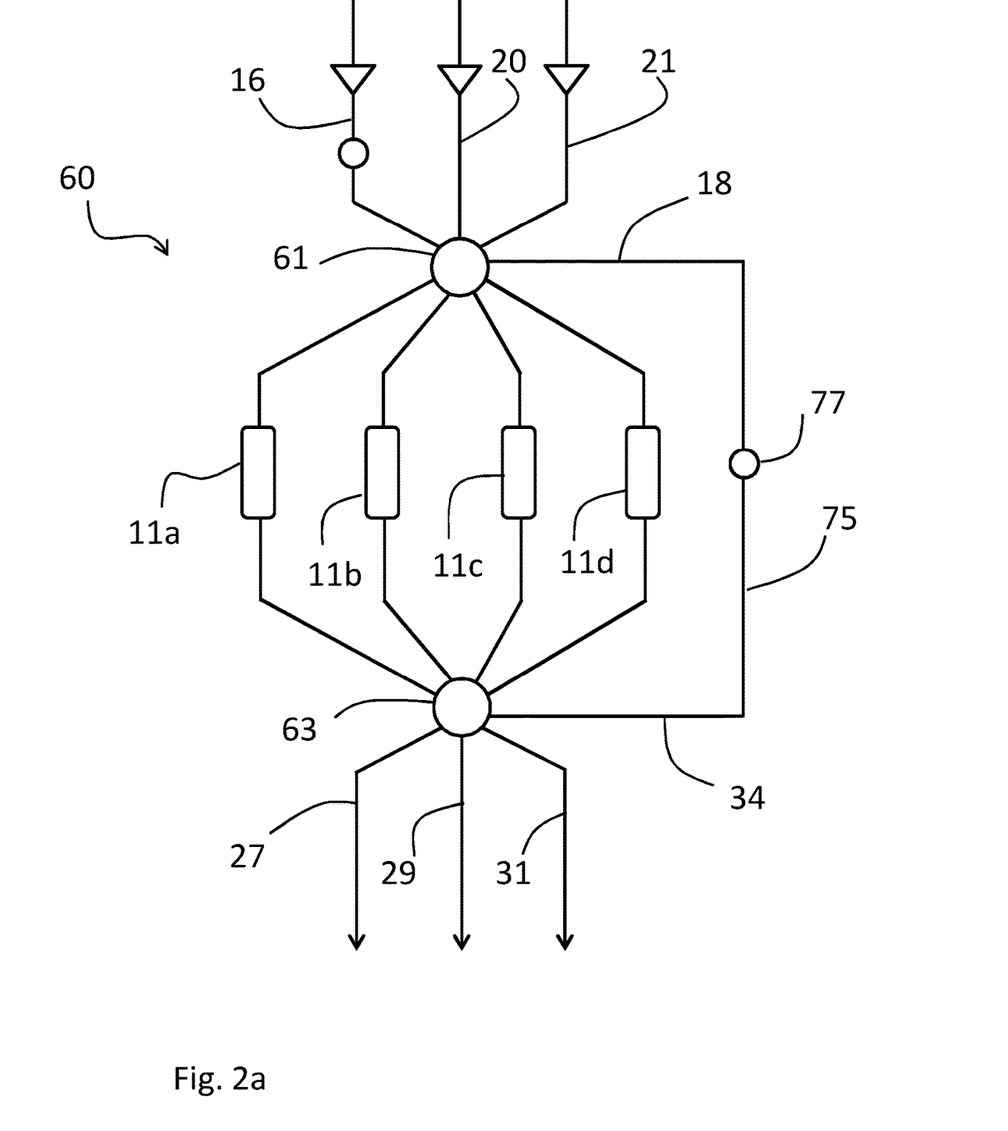
FIG. 2a shows schematically a chromatography system with four columns in which the rotary valve of the invention can be used.

FIG. 2a shows schematically a chromatography system 60 in which a rotary valve according to the invention can be provided. In this embodiment four columns 11a, 11b, 11c, 11d are connected in a simulated moving bed system. However the number of columns can be varied. The rotary valve according to the invention can for example be used for a system with 3 columns or more than four columns which will be discussed in more detail below. A column inlet rotary valve 61 according to the invention is connected to the inlets of the columns in the system. This column inlet rotary valve 61 is connected to the inlets of all the columns in the system and furthermore to a first inflow 16 (in this embodiment representing feed), a second inflow 18 (in this embodiment representing feed recirculation), a third inflow 20 (in this embodiment representing regeneration buffer) and a fourth inflow 21 (in this embodiment representing elution buffer). A rotary valve according to the invention is in this shown chromatography system provided also as a column outlet rotary valve 63. This column outlet rotary valve 63 is connected to the outlets of all the columns in the system and furthermore to a first outflow 34 (in this embodiment representing feed recirculation), a second outflow 27 (in this embodiment representing feed outlet), a third outflow 29 (in this embodiment representing regeneration outlet) and a fourth outflow 31 (in this embodiment representing elution outlet). A feed recirculation flow path 75 is provided between the column inlet rotary valve 61 and the column outlet rotary valve 63. All feed recirculation from a primary load column to a secondary load column in the simulated moving bed chromatography system will be transferred through this feed recirculation flow path 75. A detector 77 is provided in the feed recirculation flow path 75. This detector is adapted to detect an effluent signal being representative of the composition of the feed recirculation flowing through the feed recirculation flow path 75. In one embodiment the detector is a UV detector, i.e. measuring the UV absorbance of the sample. Other possible types of detectors are measuring pH, conductivity, light scattering, fluorescence, IR or visible light. This definition of detector will be the same throughout the description.

Figure 2B:
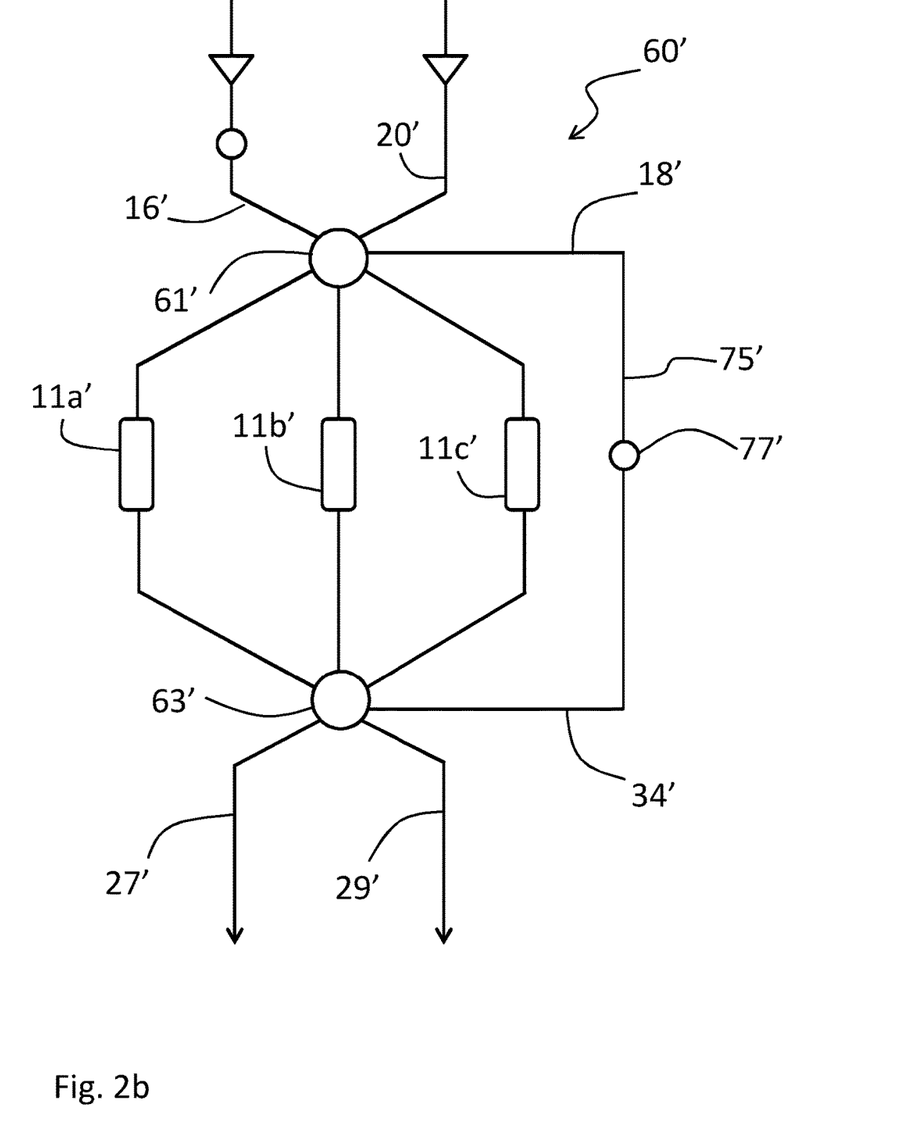
FIG. 2b shows schematically a chromatography system with three columns in which the rotary valve of the invention can be used.

FIG. 2b shows schematically a chromatography system 60' in which a rotary valve according to the invention can be provided. In this embodiment three columns 11a', 11b', 11c' are connected in a simulated moving bed system. A column inlet rotary valve 61' according to the invention is connected to the inlets of the columns in the system. This column inlet rotary valve 61' is connected to the inlets of all the columns in the system and furthermore to a first inflow 16' (in this embodiment representing feed), a second inflow 18' (in this embodiment representing feed recirculation) and a third inflow 20' (in this embodiment representing regeneration buffer and elution buffer). A rotary valve according to the invention is in this shown chromatography system provided also as a column outlet rotary valve 63'. This column outlet rotary valve 63' is connected to the outlets of all the columns in the system and furthermore to a first outflow 34' (in this embodiment representing feed recirculation), a second outflow 27' (in this embodiment representing feed outlet) and a third outflow 29' (in this embodiment representing regeneration and elution outlet). A feed recirculation flow path 75' is provided between the column inlet rotary valve 61' and the column outlet rotary valve 63'. All feed recirculation from a primary load column to a secondary load column in the simulated moving bed chromatography system will be transferred through this feed recirculation flow path 75'. A detector 77' is provided in the feed recirculation flow path 75'.

A schedule for a simulated moving bed method with feed recirculation could in one embodiment of the invention be that if the feed is directed to the first column 11a then the outflow from the first column 11a should be directed to the inlet of the second column 11b. The second column 11b hereby serves as a secondary load column and the first column serves as a primary load column. When the first column is fully loaded, which could be measured by for example UV or time, the feed is instead directed directly to the second column 11b (hereby serving as primary load column) and the outflow from the second column 11b is directed to the inlet of the third column 11c, which then serves as the secondary load column. At the same time the first column 11a is eluted by directing the elution buffer (fourth inflow 21) to the inlet of the first column 11a and let the outflow from the first column 11a be directed to the fourth outflow 31 (elution outlet). When the feed is directed directly to the third column 11c the second column is eluted and the first column is at the same time regenerated, whereby regeneration buffer is provided by the third inflow 20 to the inlet of the first column 11a and the outflow is directed to the third outflow 29 (regeneration outlet). The last step in the continuous process is that the first column 11a serves as secondary load column when the feed is directed directly to the fourth column 11d. Then the outflow from the first column 11a is directed to the feed outlet through the second outflow 27. This is a known process for simulated moving bed techniques, also called periodic counter current. The benefit with a feed recirculation is that the risk of losing any possible unbound feed is decreased and therefore the amount of sample provided to the column in the feed can be much higher than in normal chromatography. If there is any unbound feed left in the feed liquid after having passed the primary load column it will have another chance to bind in the secondary load column. This process is recycled. The inlet and outlet valves are controlled from a control system such that these above described flows are provided.

Figure 3A:
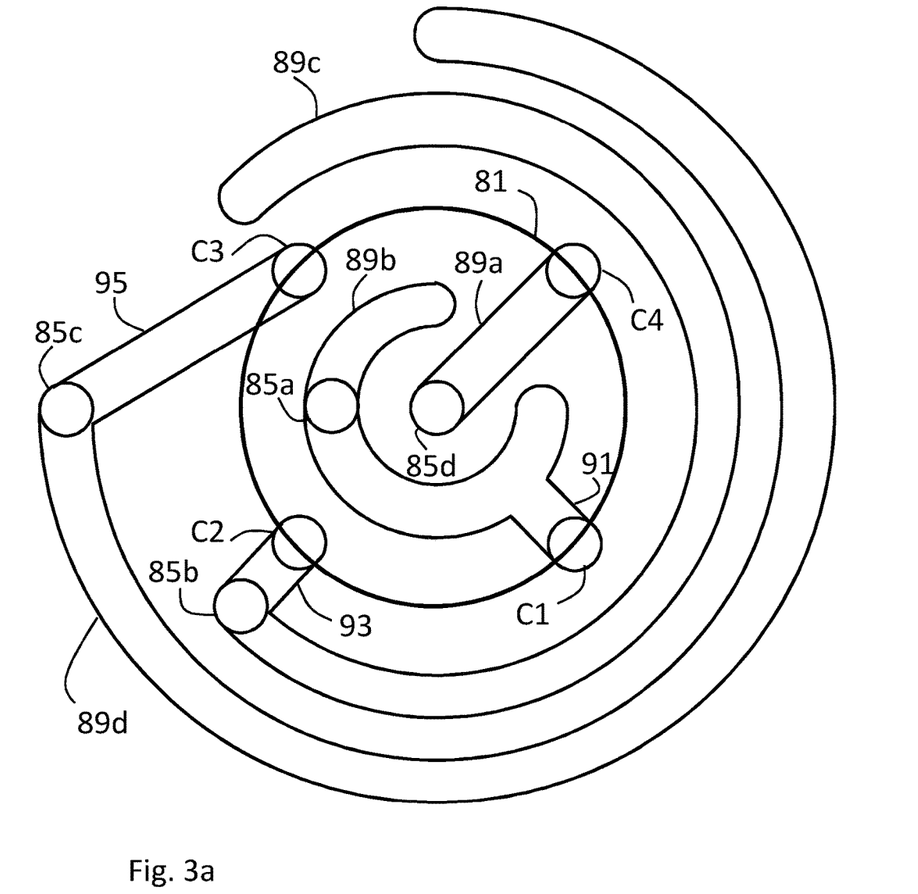
Figure 3B:
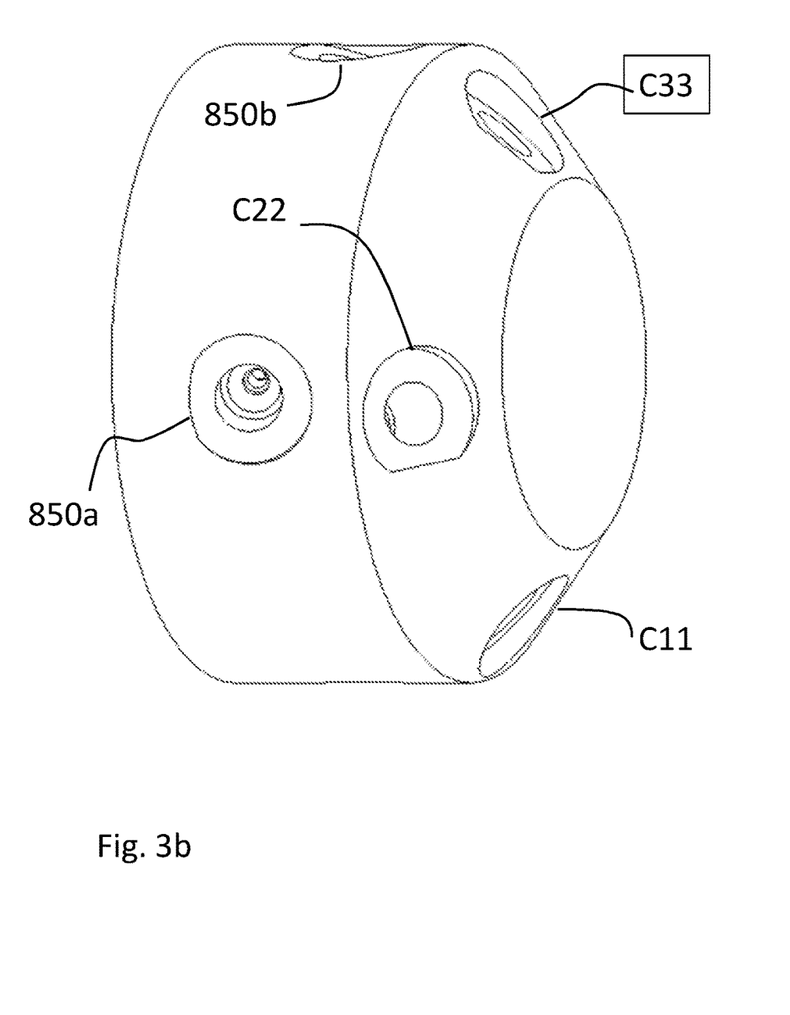
FIG. 3b shows an outside of a stator with connection ports.

FIG. 3a shows a possible design of a column inlet or outlet rotary valve 61, 63 that can be used in the embodiment of the invention shown in FIG. 2a. A rotary valve comprises a stator with an inner stator face, and a rotor with an inner rotor face arranged in sealing contact with the inner stator face. The rotor is rotatably movable to a plurality of rotor positions about a rotational axis relative to the inner stator face. The stator comprises a plurality of connection ports each being in fluidic contact with a corresponding valve orifice at the inner stator face and the rotor comprises two or more interconnection paths for selective fluidic interconnection of said valve orifices with respect to the rotor position. In FIG. 3a the valve orifices on the inner stator face and the interconnecting paths on the rotor are shown in the same view. In FIG. 3b connection ports on the outside of a stator is shown. However these connection ports can be positioned in any wanted way. In this embodiment of the rotary valve used in FIG. 2a the stator comprises four primary valve orifices C1, C2, C3, C4 each being in fluidic contact with a corresponding primary connection port (only three can be seen in the view shown in FIG. 3b, C11, C22, C33) of the stator. In this example the primary connection ports are connected to columns in the system. The stator comprises further four secondary valve orifices 85a, 85b, 85c, 85d each being in fluidic contact with a corresponding secondary connection port of the stator (only two can be seen in the view shown in FIG. 3b, 850a, 850b). In this example the secondary connection ports are connected to inflows (for inlet rotary valve) or outflows (for outlet rotary valve) in the system shown in FIG. 2a. The interconnection paths in the rotor are arranged to, in the different rotor positions interconnect the primary valve orifices C1, C2, C3, C4 with the secondary valve orifices 85a, 85b, 85c, 85d such that all secondary valve orifices can be connected one at the time to each primary valve orifice by rotating the rotor into the different rotor positions.

In FIG. 3a stator valve orifices are shown by circles. There are four primary valve orifices denoted C1, C2, C3 and C4. The corresponding primary connection ports of the stator are in this embodiment connections to the columns in the system. Furthermore there are four secondary valve orifices, a first secondary valve orifice 85a, a second secondary valve orifice 85b, a third secondary valve orifice 85c and a fourth secondary valve orifice 85d. For an inlet rotary valve 61 the first secondary valve orifice 85a will in the embodiment shown in FIG. 2a be connected to feed through a corresponding first secondary connection port in the stator, the second secondary valve orifice 85b will be connected to feed recirculation through a corresponding second secondary connection port in the stator, the third secondary valve orifice 85c will be connected to regeneration through a corresponding third secondary connection port in the stator and the fourth secondary valve orifice 85d will be connected to elution through a corresponding fourth secondary connection port in the stator. If the rotary valve is used as outlet rotary valve 63 the first secondary valve orifice 85a will be connected to feed recirculation as discussed above through a first secondary connection port in the stator, the second secondary valve orifice 85b will be connected to feed outlet through a second secondary connection port in the stator, the third secondary valve orifice 85c will be connected to regeneration outlet through a third secondary connection port of the stator and the fourth secondary valve orifice 85d will be connected to elution outlet as discussed above through a fourth secondary connection port of the stator.

However the order and organisation and naming of these secondary valve orifices could be varied as long as the simulated moving bed process is followed from rotation of the rotor of the rotary valve. In the rotor of the rotary valve there are in this embodiment provided rotor interconnection paths as grooves. In this embodiment three of these rotor interconnection paths are provided partly along a part of a circle. The rotor interconnection paths are arranged such that each one of the primary valve orifices C1, C2, C3, C4 is connected to one each of the secondary valve orifices 85a,b,c,d in each rotational position of the rotary valve. By rotating the rotor of the rotary valve into four different positions the connections of inflows/outflows (FIG. 2a) to the columns will be shifted according to the simulated moving bed process. This is also shown in FIGS. 4a-4d. I.e.:

In a first rotational position (FIG. 4a) of the rotary valve the first primary valve orifice C1 is connected to the first secondary valve orifice 85a, the second primary valve orifice C2 is connected to the second secondary valve orifice 85b, the third primary valve orifice C3 is connected to the third secondary valve orifice 85c and the fourth primary valve orifice C4 is connected to the fourth secondary valve orifice 85d.

In a second rotational position (FIG. 4b) of the rotary valve the first primary valve orifice C1 is connected to the fourth secondary valve orifice 85d, the second primary valve orifice C2 is connected to the first secondary valve orifice 85a, the third primary valve orifice C3 is connected to the second secondary valve orifice 85b and the fourth primary valve orifice C4 is connected to the third secondary valve orifice 85c.

In a third rotational position (FIG. 4c) of the rotary valve the first primary valve orifice C1 is connected to the third secondary valve orifice 85c, the second primary valve orifice C2 is connected to the fourth secondary valve orifice 85d, the third primary valve orifice C3 is connected to the first secondary valve orifice 85a and the fourth primary valve orifice C4 is connected to the second secondary valve orifice 85b.

In a fourth rotational position (FIG. 4d) of the rotary valve the first primary valve orifice C1 is connected to the second secondary valve orifice 85b, the second primary valve orifice C2 is connected to the third secondary valve orifice 85c, the third primary valve orifice C3 is connected to the fourth secondary valve orifice 85d and the fourth primary valve orifice C4 is connected to the first secondary valve orifice 85a.

In this shown embodiment of the invention the four primary valve orifices C1, C2, C3, C4 are provided with equal distance from each other around a primary circle 81 on the stator. The four secondary valve orifices 85a,b,c,d are positioned on the inner stator face such that they in different rotor positions can connect to each one of the four primary valve orifices in an order suitable for the simulated moving bed process as described above. In the embodiment shown in FIGS. 3a and 4 the secondary valve orifices positions for two of these are provided inside the primary circle 81 on which the primary valve orifices are provided and one of these in the centre of the stator. In this example it is shown that the fourth secondary valve orifice 85d position is provided in the centre of the stator and the first secondary valve orifice 85a position is provided between the centre and the primary circle 81. The other two secondary valve orifices, here named second secondary valve orifice 85b and third secondary valve orifice 85c, are provided at different radius from the centre outside the primary circle 81 and also separated in another direction. The design of the rotor interconnection paths in the rotor should then be provided such that all four primary valve orifices can be connected to each one of the secondary valve orifices 85a,b,c,d in different rotor positions. To achieve this at least three of the rotor interconnection paths need to comprise parts that are bent. In this embodiment a first rotor interconnection path 89a is provided such that it in all rotor positions connects the fourth secondary valve orifice 85d with one of the primary valve orifices C1, C2, C3, C4. A second rotor interconnection path 89b is provided such that it in all rotor positions connects the first secondary valve orifice 85a with one of the primary valve orifices C1, C2, C3, C4. To achieve this the second rotor interconnection path 89b is provided partly as a bended groove along a part of a circle inside the primary circle 81. Furthermore the second rotor interconnection path 89b comprises an extending part 91 extending out form the bended part to the position of the primary circle 81 in order to be able to connect the first secondary valve orifice 85a with all the primary valve orifices C1, C2, C3, C4, one in each rotor position. A third rotor interconnection path 89c is provided such that it in all rotor positions connects the second secondary valve orifice 85b with one of the primary valve orifices C1, C2, C3, C4. To achieve this the third rotor interconnection path 89c is provided partly as a bended groove along a part of a circle outside the primary circle 81. Furthermore the third rotor interconnection path 89c comprises an extending part 93 extending inwardly form the bended part to the position of the primary circle 81 in order to be able to connect the second secondary valve orifice 85b with all the primary valve orifices C1, C2, C3, C4, one in each rotor position. A fourth rotor interconnection path 89d is provided such that it in all rotor positions connects the third secondary valve orifice 85c with one of the primary valve orifices C1, C2, C3, C4. To achieve this the fourth rotor interconnection path 89d is provided partly as a bended groove along a part of a circle outside the primary circle 81 and outside the third rotor interconnection path 89c. Furthermore the fourth rotor interconnection path 89d comprises an extending part 95 extending inwardly form the bended part to the position of the primary circle 81 in order to be able to connect the third secondary valve orifice 85c with all the primary valve orifices C1, C2, C3, C4, one in each rotor position. This extending part 95 needs to be bended or declined for allowing all connections properly. The functions and positions of the different stator valve orifice can be varied as long as the simulated moving bed process as described above is achieved through the different rotor positions.

With an inlet rotary valve and an outlet rotary valve as shown in FIG. 3a the simulated moving bed system 60 shown in FIG. 2a can be operated and feed recirculation can be provided through one single feed recirculation flow path 75. This feed recirculation flow path 75 is therefore connected to the second secondary valve orifice 85b of the inlet rotary valve 61 and to the first secondary valve orifice 85a of the outlet rotary valve 63.

Figure 3C:
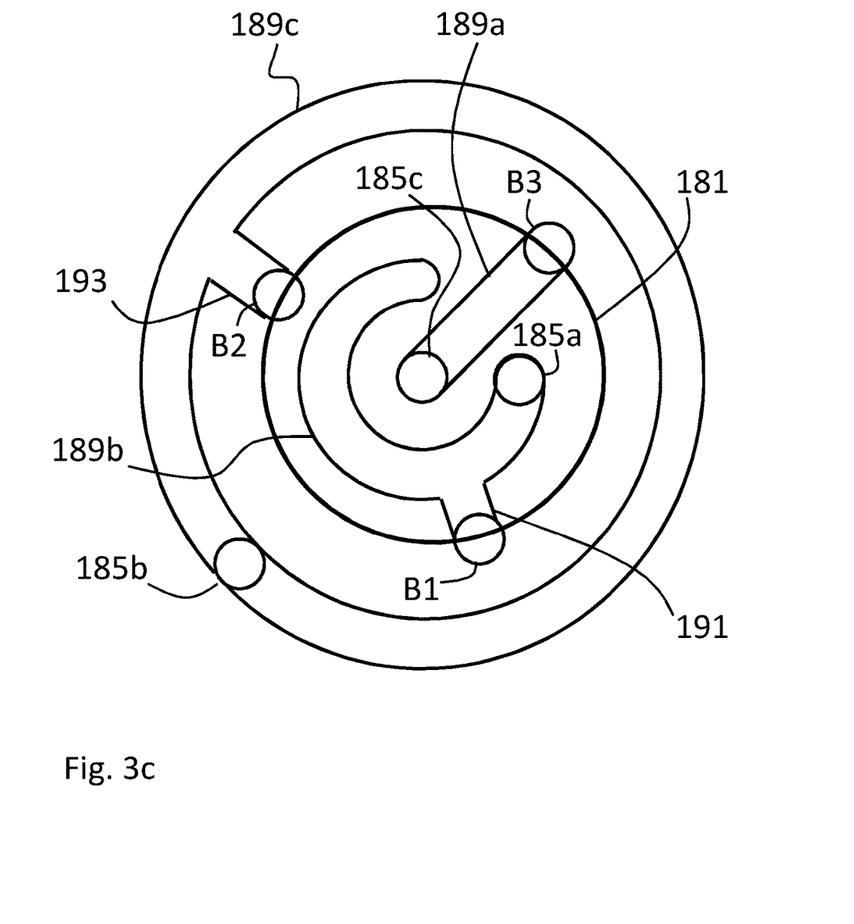
FIG. 3c shows a rotary valve according to one embodiment of the invention that can be used in the chromatography system of FIG. 2b.
Figure 4A:
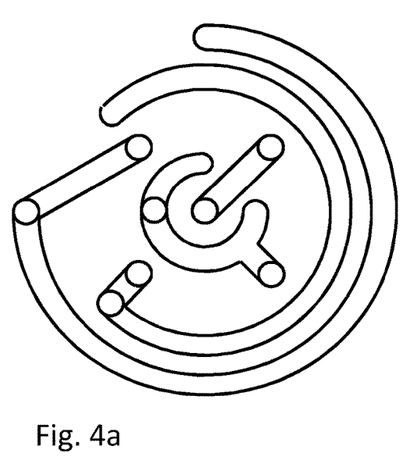
Figure 4B:
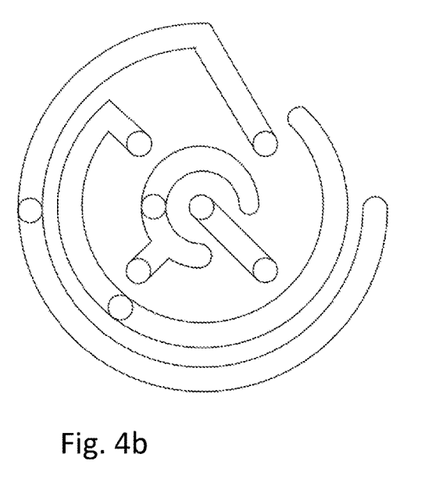
Figure 4C:
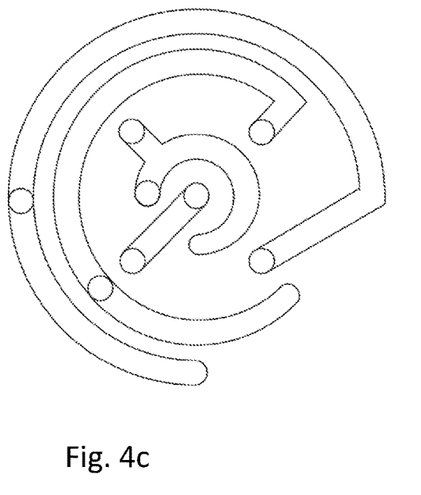
Figure 4D:
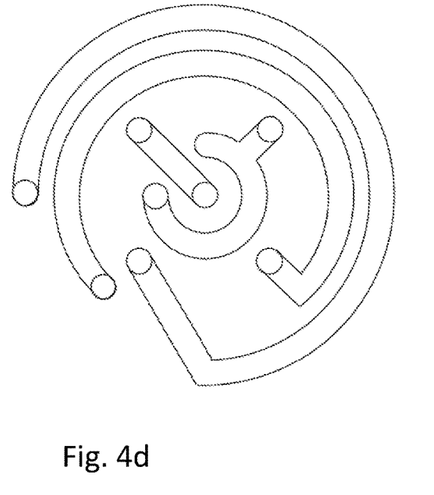

FIG. 3c shows a possible design of a column inlet or outlet rotary valve 61', 63' that can be used in the embodiment of the invention shown in FIG. 2b. In FIG. 3c the valve orifices on the inner stator face and the interconnecting paths on the rotor are shown in the same view. In this embodiment of the rotary valve used in FIG. 2b the stator comprises three primary valve orifices B1, B2, B3 each being in fluidic contact with a corresponding primary connection port of the stator. In this example the primary connection ports are connected to columns in the system. The stator comprises further three secondary valve orifices 185a, 185b, 185c each being in fluidic contact with a corresponding secondary connection port of the stator. In this example the secondary connection ports are connected to inflows (for inlet rotary valve) or outflows (for outlet rotary valve) in the system shown in FIG. 2b. The interconnection paths in the rotor are arranged to, in the different rotor positions interconnect the primary valve orifices B1, B2, B3 with the secondary valve orifices 185a, 185b, 185c such that all secondary valve orifices can be connected one at the time to each primary valve orifice by rotating the rotor into the different rotor positions.

In FIG. 3c stator valve orifices are shown by circles. For an inlet rotary valve 61' the first secondary valve orifice 185a will in the embodiment shown in FIG. 2b be connected to feed through a corresponding first secondary connection port in the stator, the second secondary valve orifice 185b will be connected to feed recirculation through a corresponding second secondary connection port in the stator, the third secondary valve orifice 185c will be connected to regeneration and to elution through a corresponding third secondary connection port in the stator. If the rotary valve is used as outlet rotary valve 63' the first secondary valve orifice 185a will be connected to feed recirculation as discussed above through a first secondary connection port in the stator, the second secondary valve orifice 185b will be connected to feed outlet through a second secondary connection port in the stator, the third secondary valve orifice 185c will be connected to regeneration and to elution outlet through a third secondary connection port of the stator as discussed above.

However the order and organisation and naming of these secondary valve orifices could be varied as long as the simulated moving bed process is followed from rotation of the rotor of the rotary valve. In the rotor of the rotary valve there are in this embodiment provided rotor interconnection paths as grooves. In this embodiment two of these rotor interconnection paths are provided partly along at least a part of a circle. The rotor interconnection paths are arranged such that each one of the primary valve orifices B1, B2, B3 is connected to one each of the secondary valve orifices 185a,b,c in each rotational position of the rotary valve. By rotating the rotor of the rotary valve into three different positions the connections of inflows/outflows (FIG. 2b) to the columns will be shifted according to the simulated moving bed process.

In this shown embodiment of the invention the three primary valve orifices B1, B2, B3 are provided with equal distance from each other around a primary circle 181 on the stator. The three secondary valve orifices 185a,b,c are positioned on the inner stator face such that they in different rotor positions can connect to each one of the three primary valve orifices in an order suitable for the simulated moving bed process as described above. In the embodiment shown in FIG. 3c the secondary valve orifices positions for two of these are provided inside the primary circle 181 on which the primary valve orifices are provided and one of these in the centre of the stator. In this example it is shown that the third secondary valve orifice 185c position is provided in the centre of the stator and the first secondary valve orifice 185a position is provided between the centre and the primary circle 181. The last secondary valve orifice, here named second secondary valve orifice 185b, is provided outside the primary circle 181. The design of the rotor interconnection paths in the rotor should then be provided such that all three primary valve orifices can be connected to each one of the secondary valve orifices 185a,b,c in different rotor positions. To achieve this at least two of the rotor interconnection paths need to comprise parts that are bent. In this embodiment a first rotor interconnection path 189a is provided such that it in all rotor positions connects the third secondary valve orifice 185c with one of the primary valve orifices B1, B2, B3. A second rotor interconnection path 189b is provided such that it in all rotor positions connects the first secondary valve orifice 185a with one of the primary valve orifices B1, B2, B3. To achieve this the second rotor interconnection path 189b is provided partly as a bended groove along a part of a circle inside the primary circle 181. Furthermore the second rotor interconnection path 189b comprises an extending part 191 extending out form the bended part to the position of the primary circle 181 in order to be able to connect the first secondary valve orifice 185a with all the primary valve orifices B1, B2, B3 one in each rotor position. A third rotor interconnection path 189c is provided such that it in all rotor positions connects the second secondary valve orifice 185b with one of the primary valve orifices B1, B2, B3. To achieve this the third rotor interconnection path 189c is in this embodiment provided as a complete circle outside the primary circle 181. Furthermore the third rotor interconnection path 189c comprises an extending part 193 extending inwardly form the bended part to the position of the primary circle 181 in order to be able to connect the second secondary valve orifice 185b with all the primary valve orifices B1, B2, B3 one in each rotor position. The functions and positions of the different stator valve orifices can be varied as long as the simulated moving bed process as described above is achieved through the different rotor positions.

With an inlet rotary valve and an outlet rotary valve as shown in FIG. 3c the simulated moving bed system 60' shown in FIG. 2b can be operated and feed recirculation can be provided through one single feed recirculation flow path 75'. This feed recirculation flow path 75' is therefore connected to the second secondary valve orifice 185b of the inlet rotary valve 61' and to the first secondary valve orifice 185a of the outlet rotary valve 63'.

Figure 5:
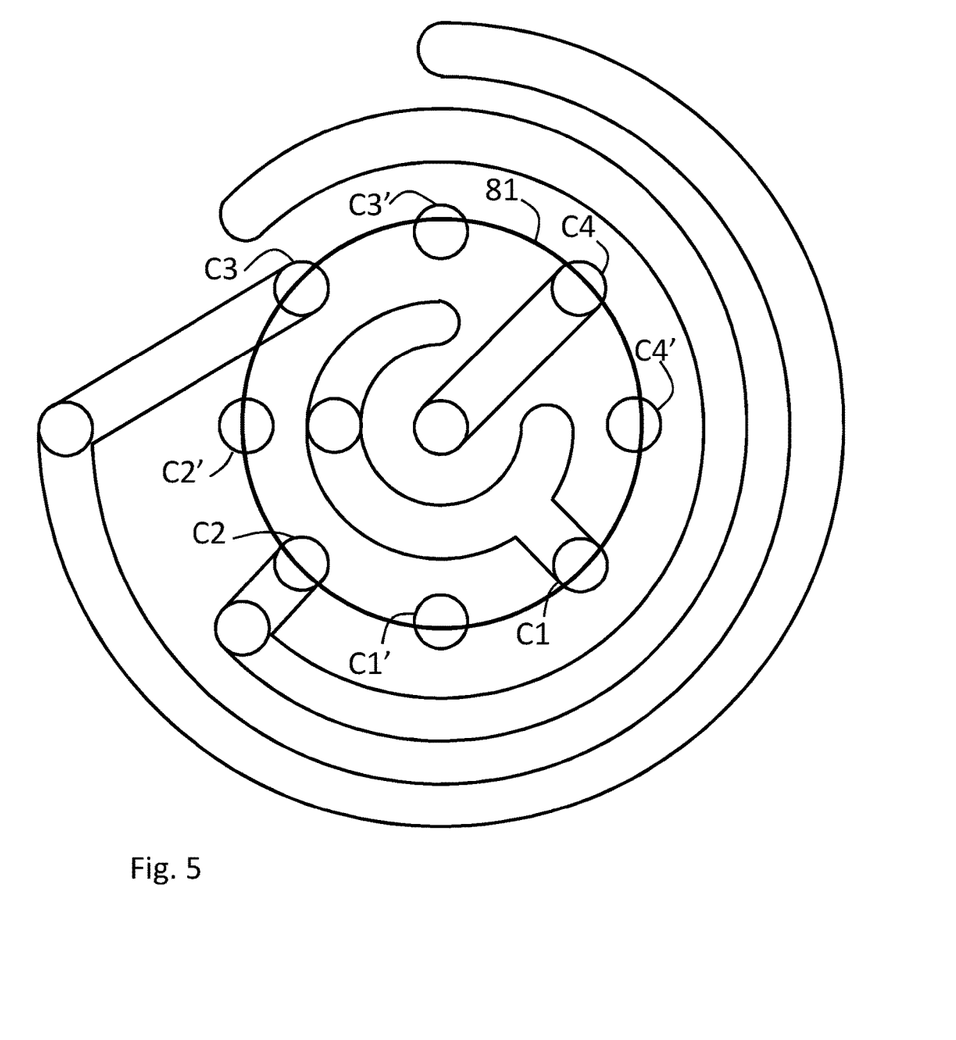
FIG. 5 shows a rotary valve according to one embodiment of the invention where column bypass has been included.

FIG. 5 shows the design of another embodiment of a rotary valve that can be used in the embodiment shown in FIG. 2a. In this embodiment the function of column bypass has been included. To provide this four extra primary valve orifices C1', C2', C3', C4' are provided in between the primary valve orifices C1, C2, C3, C4 on the primary circle 81. Flow connections can be provided between the inlet and outlet valves such that fluid can be pumped through the system without entering the columns. This can be used for system wash. The design of the rotor and stator is beside this much the same as described for the previous embodiments and will not be described further here.

Figure 6:
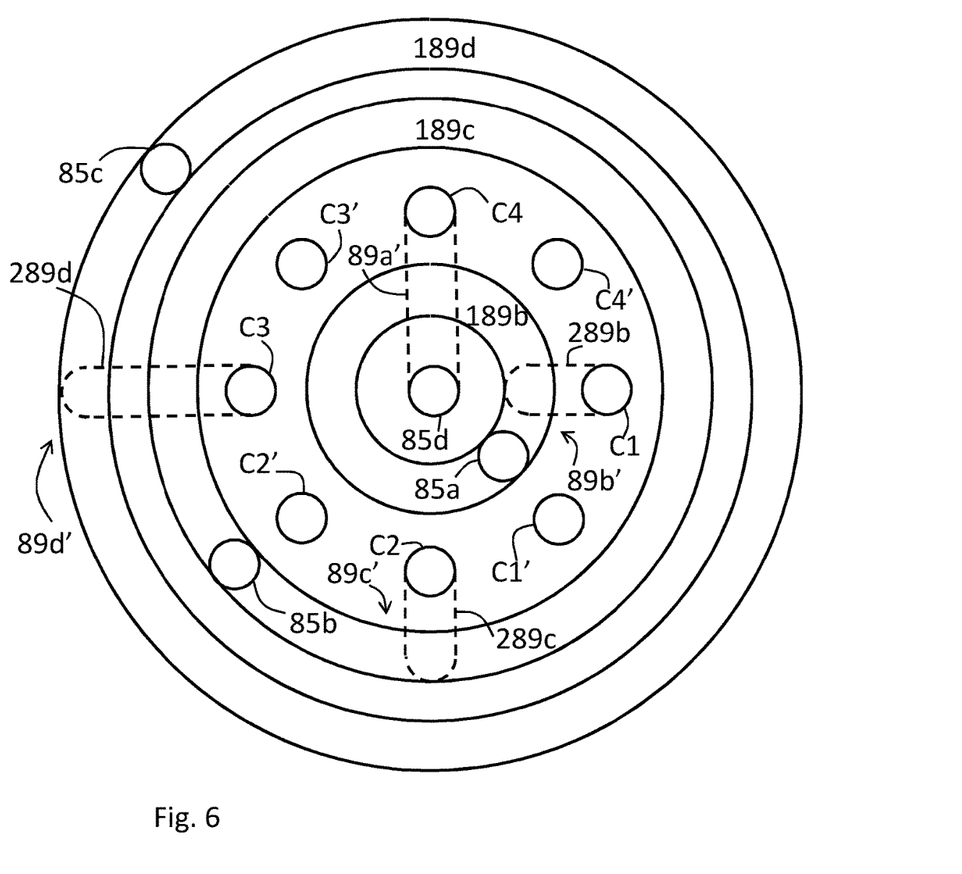
FIG. 6 shows a rotary valve according to another embodiment of the invention that can be used in the chromatography system of FIG. 2.

FIG. 6 shows another embodiment of the rotary valve shown in FIGS. 3a and 5. This embodiment could be provided with or without the bypass function as described in relation to FIG. 5. Here the four extra primary valve orifices C1', C2', C3' and C4' are shown but they could also be omitted. Four primary valve orifices C1, C2, C3 and C4 are shown in this embodiment. They are provided with equal distances around a primary circle 81 in the same way as described for the embodiment shown in FIG. 3a (however in this embodiment this primary circle 81 actually can be provided at any radial distance from the center which will be further discussed below). The secondary valve orifices 85a, 85b, 85c, 85d of the stator are also provided at the same positions as in the embodiment described with reference to FIG. 3a. The difference is that the rotor interconnection paths have been divided into circular grooves on the inner rotor face and radial channels which are drilled within the rotor. Hereby the circular grooves will not interfere with the radial channels and the circular grooves can be provided as complete circles. In more detail a first rotor interconnection path 89a' is provided as a first radial channel connecting the fourth primary valve orifice C4 and the fourth secondary valve orifice 85d. This channel is provided below the surface of the rotor and below the bottom of the circular grooves which will be further described below. A second rotor interconnection path 89b' comprises two parts: one second circular groove part 189b which circular groove is provided inside the primary circle 8lat the same distance from the center as the first secondary valve orifice 85a and one second radial channel part 289b. The second radial channel part 289b is provided from the primary circle 81 to the position of the first secondary valve orifice 85a but drilled within the rotor. A third rotor interconnection path 89c' comprises also two parts: one third circular groove part 189c which circular groove part is provided outside the primary circle 81a t the same distance from the center as the second secondary valve orifice 85b and one third radial channel part 289c. The third radial channel part 289c is provided from the third circular groove part 189c to the primary circle 81 and it is drilled within the rotor. A fourth rotor interconnection path 89d' comprises also two parts: one fourth circular groove part 189d which circular groove part is provided outside the third circular groove part 189c at the same distance from the center as the third secondary valve orifice 85c and one fourth radial channel part 289d. The fourth radial channel part 289d is provided from the fourth circular groove part 189d to the primary circle 81 and it is drilled within the rotor. Hereby the circular grooves can be provided as complete circles unlike the embodiment shown in FIG. 3. As also shown in FIG. 6 bypass can be provided also to this embodiment by including bypass column connections on the primary circle 81, C1', C2', C3', C4'. With this method of using drilled channels inside the rotor the primary valve orifices C1, C2, C3, C4 can be provided at any radial distance as wanted because the problem of channels interfering each other is eliminated.

Figure 7:
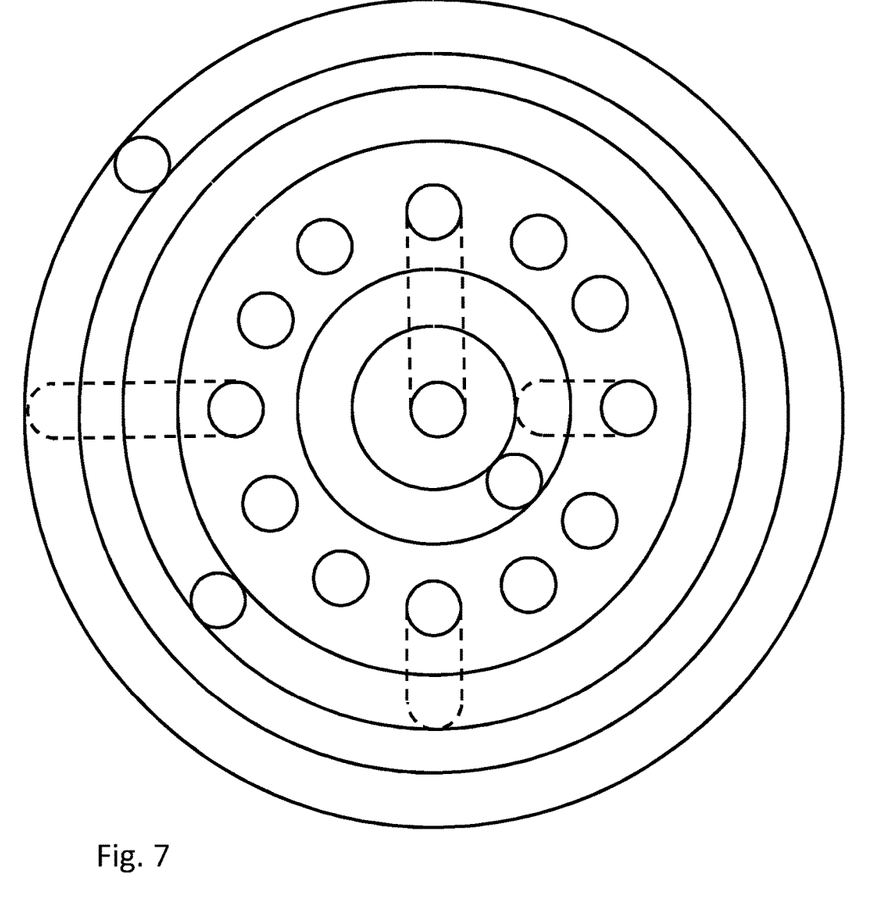
FIG. 7 shows a rotary valve according to another embodiment of the invention where an additional set of four columns can be used.

FIG. 7 shows another embodiment of the invention which embodiment is similar to the embodiment described with reference to FIG. 6. The only difference is that another set of primary valve orifices has been provided on the primary circle 81. In this way a second set of four columns can be connected to the system. If a first set of four columns first is used for a number of chromatography cycles a second set of four columns can then be used when the first set needs to be replaced or cleaned. This provides improved efficiency to the system. Furthermore in this shown embodiment column bypass is also provided.

The rotary valve according to the invention can also be adopted for another number of connected columns according to the same principles as disclosed in the embodiments described above. For example in the embodiment shown in FIG. 6, comprising circular grooves and radial channels additional circular grooves and radial channels are simply added for additional columns in the system. A system using five columns could for example be used if the regeneration step is divided into two steps, one for column cleaning in place and one for equilibration. Even six columns could be used in a system if elution is divided into wash and elution.

Another possibility would be to use a rotary valve according to the invention as either inlet or outlet valve and use other conventional valves for the other sides of the columns, i.e. conventional separate outlet valves for the column outlets if a rotary inlet valve according to the invention is used for the inlet side or conventional separate inlet valves for the columns if a rotary outlet valve according to the invention is used. This should also be covered by this invention.

The invention claimed is:

1. A rotary valve comprising a stator with an inner stator face, and a rotor with an inner rotor face arranged in sealing contact with the inner stator face, the rotor is rotatably movable to a plurality of rotor positions about a rotational axis relative to the inner stator face, the stator comprises a plurality of connection ports each being in fluidic contact with a corresponding valve orifice at the inner stator face and the rotor comprises two or more rotor interconnection paths for selective fluidic interconnection of said valve orifices with respect to the rotor position, wherein the stator comprises at least three primary connection ports and at least three secondary connection ports with one of the secondary connection ports located at the radial center of the stator, and wherein the rotor interconnection paths are arranged to:

in the different rotor positions, interconnect the primary connection ports with the secondary connection ports such that all of said at least three secondary connection ports can be connected one at a time to each of said at least three primary connection ports by rotating the rotor into the different rotor positions.

2. The rotary valve according to claim 1, wherein by rotating the rotor, the interconnections of the primary connection ports with the secondary connection ports will be shifted according to a simulated moving bed process.

3. The rotary valve according to claim 1, wherein at least two of the rotor interconnection paths are partly bending grooves.

4. The rotary valve according to claim 1, wherein the rotor interconnection paths are arranged to:

in a first rotor position interconnect a first primary valve orifice with a first secondary valve orifice, a second primary valve orifice with a second secondary valve orifice, a third primary valve orifice with a third secondary valve orifice and a fourth primary valve orifice with a fourth secondary valve orifice, in a second rotor position interconnect the first primary valve orifice with the fourth secondary valve orifice, the second primary valve orifice with the first secondary valve orifice, the third primary valve orifice with the second secondary valve orifice and the fourth primary valve orifice with the third secondary valve orifice, in a third rotor position interconnect the first primary valve orifice with the third secondary valve orifice, the second primary valve orifice with the fourth secondary valve orifice, the third primary valve orifice with the first secondary valve orifice and the fourth primary valve orifice with the second secondary valve orifice, in a fourth rotor position interconnect the first primary valve orifice with the second secondary valve orifice, the second primary valve orifice with the third secondary valve orifice, the third primary valve orifice with the fourth secondary valve orifice and the fourth primary valve orifice with the first secondary valve orifice.

5. The rotary valve according to claim 1, wherein at least two of the rotor interconnection paths each comprises one circular groove and one radial channel.

6. The rotary valve according to claim 5, wherein the circular grooves are concentrically positioned around the centre of the rotary valve and have different radii corresponding to the different radius at which the secondary valve orifices are provided and the radial channels are provided reaching out from their respective circular grooves to the positions of the primary valve orifices.

7. The rotary valve according to claim 1, wherein extra primary connection ports and valve orifices are provided in the stator in order to allow column bypass and/or additional set up of columns.

8. The rotary valve according to claim 1, wherein the rotor interconnection paths are grooves in the rotor with one groove being a straight radial channel and the rest of the grooves being at least partly bending and the straight radial channel is in fluid communication with the secondary connection port located at the radial center of the stator.

9. A chromatography system comprising at least three chromatography columns, said system further comprising:
    a column inlet rotary valve connected to the inlets of at least three columns in the system and to at least three inflows and
    a column outlet rotary valve connected to the outlets of at least three columns in the system and to at least three outflows, and
    a feed recirculation flow path in which feed recirculation from the outlet of the column presently serving as primary load column in a chromatography process to the inlet of the column presently serving as secondary load column is transferred,
    wherein said feed recirculation flow path transfers the feed recirculation from all the columns in the system serving as primary load columns and wherein said feed recirculation flow path is connected to the inlets and outlets of the columns through the column inlet and column outlet rotary valves.

10. The chromatography system according to claim 9, wherein said inlets of said chromatography columns are connected one to each of at least three primary connection ports of the inlet rotary valve and said outlets of said chromatography columns are connected one to each of at least three primary connection ports of the outlet rotary valve and said inflows are connected one to each of at least three secondary connection ports of the inlet rotary valve and said outflows are connected one to each of at least three secondary connection ports of the outlet rotary valve and wherein rotor interconnection paths are provided such that each of said at least three inflows can be connected one at a time with each of said at least three column inlets through the inlet rotary valve and each of said at least three outflows can be connected one at a time with each of said at least three column outlets through the outlet rotary valve and by rotating the rotors, the inflows to the column inlets and the outflows to the column outlets will be shifted according to a simulated moving bed process.

11. The chromatography system according to claim 9, wherein the feed recirculation flow path comprises a detector.

12. The chromatography system according to claim 10, wherein the rotor interconnection paths are grooves in the rotor with one groove being a straight radial channel and the rest of the grooves being at least partly bending and wherein one of the secondary connection ports is located at the radial center of the stator and in fluid communication with the straight radial channel.

13. The chromatography system according to claim 10, wherein at least two of the rotor interconnection paths each comprises one circular groove and one radial channel.

14. A rotary valve comprising a stator with an inner stator face, and a rotor with an inner rotor face arranged in sealing contact with the inner stator face, the rotor is rotatably movable to a plurality of rotor positions about a rotational axis relative to the inner stator face, the stator comprises a plurality of connection ports each being in fluidic contact with a corresponding valve orifice at the inner stator face and the rotor comprises two or more rotor interconnection paths for selective fluidic interconnection of said valve orifices with respect to the rotor position,
    wherein the rotor interconnection paths are grooves in the rotor with one groove being a straight radial channel and the rest of the grooves being at least partly bending,
    wherein the stator comprises at least three primary connection ports and at least three secondary connection ports, and
    wherein the rotor interconnection paths are arranged to:
    in the different rotor positions, interconnect the primary connection ports with the secondary connection ports such that all of said at least three secondary connection ports can be connected one at a time to each of said at least three primary connection ports by rotating the rotor into the different rotor positions.

15. The rotary valve according to claim 14, wherein by rotating the rotor, the interconnections of the primary connection ports with the secondary connection ports will be shifted according to a simulated moving bed process.

16. The rotary valve according to claim 14, wherein there are three interconnection paths.

17. The rotary valve according to claim 14, wherein the rotor interconnection paths are arranged to:
    in a first rotor position interconnect a first primary valve orifice with a first secondary valve orifice, a second primary valve orifice with a second secondary valve orifice, a third primary valve orifice with a third secondary valve orifice and a fourth primary valve orifice with a fourth secondary valve orifice,
    in a second rotor position interconnect the first primary valve orifice with the fourth secondary valve orifice, the second primary valve orifice with the first secondary valve orifice, the third primary valve orifice with the second secondary valve orifice and the fourth primary valve orifice with the third secondary valve orifice,
    in a third rotor position interconnect the first primary valve orifice with the third secondary valve orifice, the second primary valve orifice with the fourth secondary valve orifice, the third primary valve orifice with the first secondary valve orifice and the fourth primary valve orifice with the second secondary valve orifice,
    in a fourth rotor position interconnect the first primary valve orifice with the second secondary valve orifice, the second primary valve orifice with the third secondary valve orifice, the third primary valve orifice with the fourth secondary valve orifice and the fourth primary valve orifice with the first secondary valve orifice.

18. The rotary valve according to claim 14, wherein there are four interconnection paths.

19. The rotary valve according to claim 14, wherein extra primary connection ports and valve orifices are provided in the stator in order to allow column bypass and/or additional set up of columns.

20. The rotary valve according to claim 14, wherein one of the secondary connection ports is located in the radial center of the stator and in fluid communication with the straight radial channel.

* * * * *